United States Patent [19]
Petterson

[11] Patent Number: 6,053,318
[45] Date of Patent: Apr. 25, 2000

[54] PACKAGE FOR HOUSING A SELF-ADHESIVE BANDAGE

[76] Inventor: Tor Petterson, 31248 Palos Verdes Dr. West, Rancho Palos Verdes, Calif. 90274

[21] Appl. No.: 09/350,571

[22] Filed: Jul. 7, 1999

[51] Int. Cl.[7] .................................................. B65D 85/16
[52] U.S. Cl. ........................................ 206/440; 229/87.05
[58] Field of Search ..................... 206/438, 440, 206/812, 441; 229/87.05; 383/207

[56] References Cited

U.S. PATENT DOCUMENTS

| | | |
|---|---|---|
| 2,172,455 | 9/1939 | Samuel . |
| 4,235,337 | 11/1980 | Dotta . |
| 4,265,234 | 5/1981 | Schaar . |
| 4,418,822 | 12/1983 | Dotta . |
| 4,832,008 | 5/1989 | Gilman ..................................... 206/440 |
| 4,917,929 | 4/1990 | Heinecke . |
| 5,040,677 | 8/1991 | Tubo et al. .............................. 206/440 |
| 5,052,381 | 10/1991 | Gilbert et al. . |
| 5,074,293 | 12/1991 | Lott et al. . |
| 5,275,284 | 1/1994 | Onotsky . |
| 5,397,297 | 3/1995 | Hunter . |
| 5,628,724 | 5/1997 | Debusk et al. . |
| 5,780,048 | 7/1998 | Lee . |
| 5,840,052 | 11/1998 | Johns . |

*Primary Examiner*—Jacob K. Ackun
*Attorney, Agent, or Firm*—Sheldon & Mak; Denton L. Anderson

[57] ABSTRACT

The invention is the combination of (i) a self-adhesive bandage having opposed adhesive-coated end portions and a centralized sterile pad, and (ii) a package housing that self-adhesive bandage. The package has a rearward side and a forward side. At least the forward side has a weakened transverse line disposed off-center from the sterile pad portion of the self-adhesive bandage. When the package is pulled axially from gripping locations on opposite sides of the weakened transverse line, the forward side of the package separates at the weakened transverse line, thereby exposing the sterile pad and one adhesive-coated end portion of the self-adhesive bandage.

20 Claims, 6 Drawing Sheets fig.3 fig.4 fig.5

PACKAGE FOR HOUSING A SELF-ADHESIVE BANDAGE

FIELD OF THE INVENTION

This invention relates generally to packages for planar substrates, and, more particularly, to packages for housing self-adhesive planar substrates, such as a self-adhesive bandages.

BACKGROUND OF THE INVENTION

A variety of planar substrates must be individually packaged to preserve cleanliness of the substrate. The most common such planar substrate is a self-adhesive bandage having opposed, adhesive-coated end portions and a sterile central pad portion. To preserve the sterility of the pad portion, such self-adhesive bandages are normally packaged in individual sealed "envelopes."

Although such envelopes satisfactorily maintain the sterility of the bandage, there are several problems with the use of such envelopes. Firstly, the envelopes are frequently difficult to open. Secondly, once the envelope is opened, an additional problem is raised as to how to administer the bandage without soiling the sterile pad and without becoming entangled with the adhesive-coated ends. In almost all self-adhesive bandages on the market, the opposed adhesive-covered ends are protected with separate cover sheets. It can be exceedingly difficult to remove these cover sheets without contacting either the adhesive-covered ends or the sterile pad. The difficulty inherent in removing the protective sheets is magnified when the caregiver is wearing protective gloves. Typically, such gloves are made from a very thin material to which the adhesive on the bandage readily attaches. Accordingly, it can seem almost impossible to manipulate a simple self-adhesive bandage from package to patient by a caregiver wearing protective gloves.

Thirdly, if the injury to be bandaged is on one of the two hands of the user, all known self-adhesive bandages are extremely awkward to apply. This is because prior art self-adhesive bandages require two hands to apply. If the injury to be bandaged is on one of the user's hands, the use of two hands to apply the bandage is generally impossible.

Accordingly, there is a need for a package which eliminates the above-described problems with the prior art.

SUMMARY

The invention satisfies this need. The invention is a combination of a planar substrate and a package of housing the substrate, the substrate having a front side and a back side, the front side comprising a central portion and opposed first and second end portions, the package being elongate and having a longitudinal axis and opposed first and second distal ends, the package further comprising (a) a rearward side proximate to the back side of the substrate, (b) a forward side proximate to the front side of the substrate, (c) a forward side weakened transverse line on the forward side, so that pulling on the package along the longitudinal axis from gripping locations on opposite sides of the forward side weakened transverse line causes the forward side to separate at the forward side weakened transverse line, and wherein the forward side weakened transverse line is disposed off center with respect to the central portion of the front side of the substrate, so that a substantial portion of the central portion is exposed by separating the forward side at the forward side weakened transverse line.

In a typical embodiment, the substrate is a self-adhesive bandage having opposed adhesive-coated end portions and a sterile soft pad at its central portion.

It is also typical that the rearward side of the package have a rearward side weakened transverse line substantially aligned with the forward side weakened transverse line. Preferably, both the forward side weakened transverse line and the rearward side weakened transverse line are disposed entirely to one side of the sterile pad, so that, when the forward side and the rearward side are separated at the weakened transverse lines, the sterile pad and one of the two adhesive-coated end portions are wholly exposed.

The invention allows the user to quickly and easily open the package and apply the self-adhesive bandage to a wound without the problems inherent in prior art designs. The advantages of the invention are especially apparent where the injury to be bandaged is on one of the hands of the user. Because of the unique design of the invention, the invention can be easily applied with only one hand. This makes the bandaging of an injury on the hand of the user much easier than the application of prior art self-adhesive bandages.

DRAWINGS

These features, aspects and advantages of the present invention will become better understood with regard to the following description, appended claims and accompanying figures where:

DETAILED DESCRIPTION

The following discussion describes in detail one embodiment of the invention and several variations of that embodiment. This discussion should not be construed, however, as limiting the invention to those particular embodiments. Practitioners skilled in the art will recognize numerous other embodiments as well.

The invention is a combination 10 comprising a planar substrate 12 and a package 14 for housing the substrate 12.

The substrate 12 has a front side 16 and a back side 18. The front side 16 comprises a central portion 20 and opposed first and second end portions 22 and 24, respectively. In a typical embodiment, the substrate 12 is a self-adhesive bandage having on the front side 16 a layer of adhesive 32 on both the first and second end portions 22 and 24 and having a soft sterile pad 34 at the central portion 20.

The package 14 is elongate, having a longitudinal axis 26 and opposed first and second distal ends 28 and 30, respectively. The shape of the package is not critical. The most typical shape is generally rectangular. However, the shape can be square, round, oval, oblong, etc The package 14 comprises a rearward side 36 and a forward side 38. The rearward side 36 is disposed proximate to the back side 18 of the substrate and the forward side 38 is disposed proximate to the front side 16 of the substrate 12. Both the rearward side 36 and the forward side 38 have matching side edges 44. In most embodiments, the distal ends 28 and 30 and the matching side edges 44 will be sealed together by any one of the many suitable sealing methods known in the prior art. Sealing with an adhesive and sealing by various heating/melting processes are typical in this regard.

Where the substrate 12 is a self-adhesive bandage, the interior surface 48 of the forward side 38 of the package 14 can be coated with a low adhesive, "non-stick" film, such as tetrafluoroethylene.

At least the forward side 38 of the package 14 comprises a forward side weakened transverse line 50 disposed transverse to the longitudinal axis 26 of the package. The forward side weakened transverse line 50 is sufficiently weakened so that pulling on the package 14 along the longitudinal axis 26 from gripping locations 52 and 54 on opposite sides of the forward side weakened transverse line 50 causes the forward side 38 to separate at the forward side weakened transverse line 50.

Figures 1, 2:
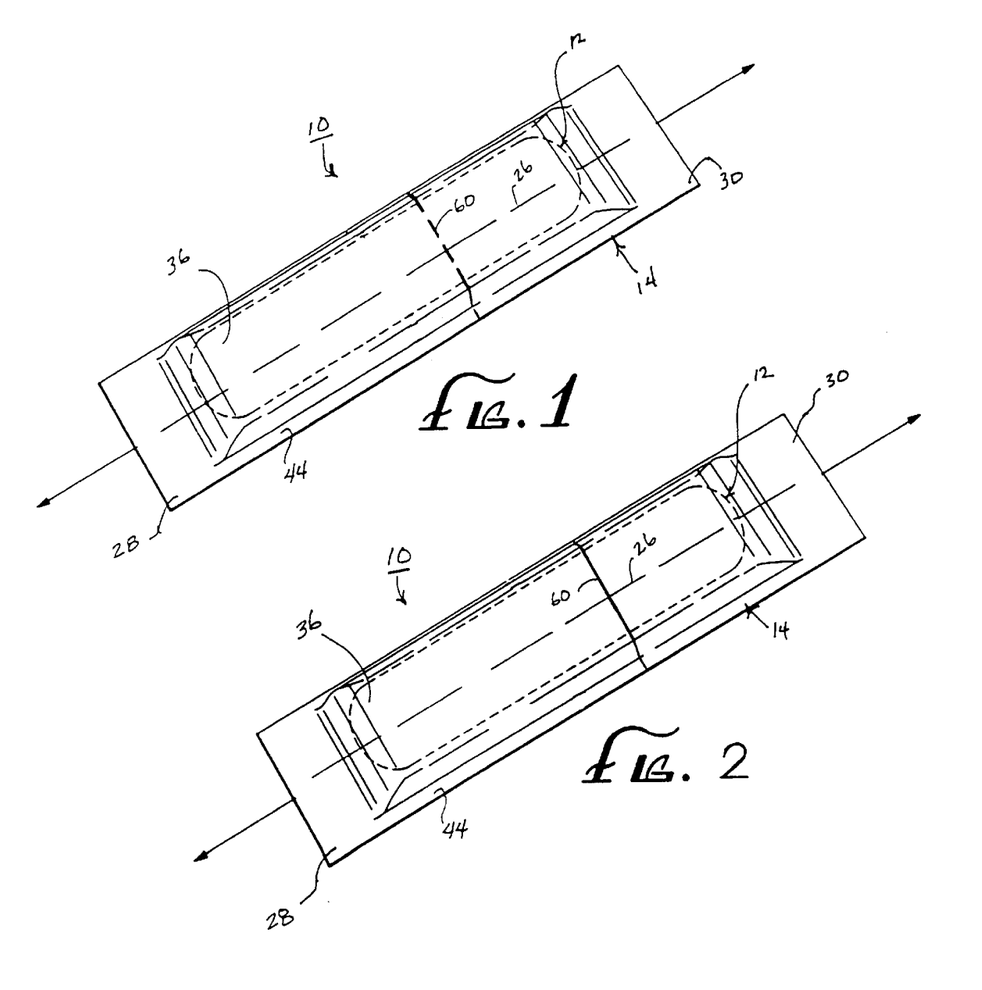
FIG. 1 is an isometric perspective view of a first combination having features of the invention.
FIG. 2 is an isometric view of the second combination having features of the invention.
Figure 3:
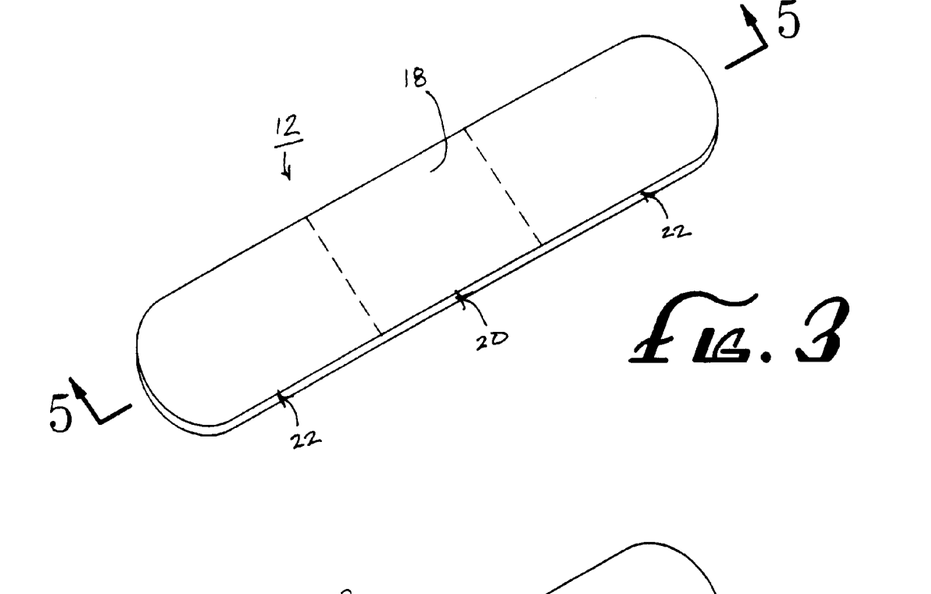
FIG. 3 is a top view of a substrate useful in the invention.
Figure 4:
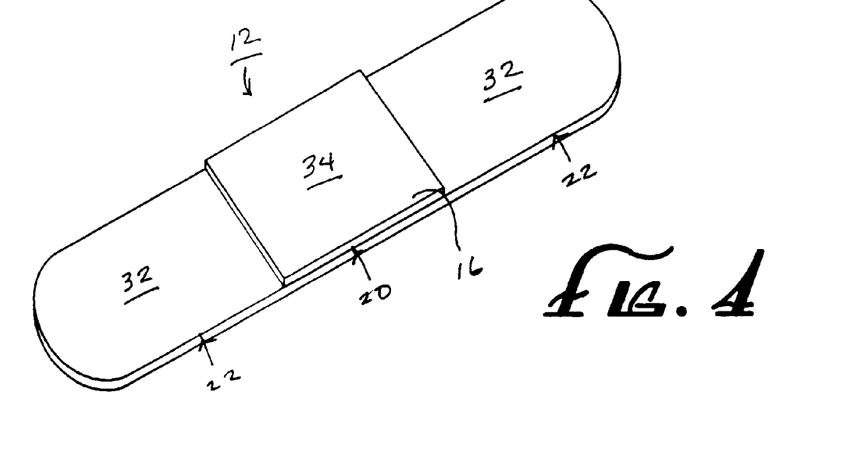
FIG. 4 is a bottom view of the substrate illustrated in FIG. 3.
Figure 5:
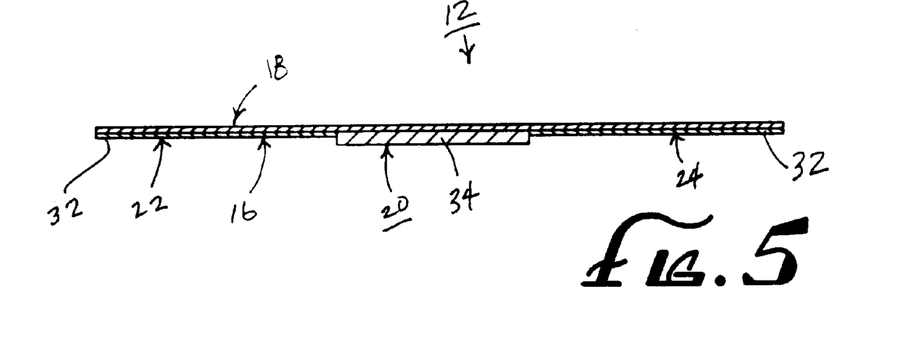
FIG. 5 is a side view of the substrate illustrated in FIG. 3.

The forward side weakened transverse line 50 can be weakened by any number of various ways known in the prior art. The forward side weakened transverse line 50 can be a perforated line as illustrated in FIG. 1. FIG. 2, on the other hand, illustrates two alternative embodiments. In a first alternative embodiment, the forward side weakened transverse line 50 is a thinned line, that is, a narrow line of material which is sufficiently thinner than the rest of the forward side material so that the forward side 38 will separate at the thinned portion when the package 14 is pulled axially from opposite sides of the forward side weakened transverse line 50. In a second alternative embodiment, the forward side weakened transverse line 50 is provided by a weakened material, that is, a material sufficiently weaker than the material in the rest of the package 14 so that, when the package 14 is stretched longitudinally from first and second gripping locations 52 and 54 disposed on opposite sides of the forward side weakened transverse line 50, the forward side 38 separates at the weakened material. In a typical embodiment, the weakened material is an adhesive which connects together a pair of otherwise separate forward side moieties 56 and 57.

In a preferred embodiment, the rearward side 36 of the package 14 also includes a rearward side weakened transverse line 60. Like the forward side weakened transverse line 50, the rearward side weakened transverse line 60 can be a perforated line, a thinned line, a weakened material or any other method of providing a weakened line known in the art.

Most preferably, both weakened transverse lines 50 and 60 are substantially perpendicular to the longitudinal axis 26 of the package 14.

It is also preferable that both the forward side weakened transverse line 50 and the rearward side weakened transverse line 60 are aligned in close proximation to one another, so that, when the package 14 is pulled along the longitudinal axis 26 from gripping locations 52 and 54 on opposite sides of the weakened transverse lines 50 and 60, the entire package 14 separates at the two weakened transverse lines 50 and 60 into two separate package moieties 58 and 59.

An important feature of the invention is the fact that the forward side weakened transverse line 50, and preferably also the rearward side weakened transverse line 60, are disposed off-center with respect to the central portion 20 of the front side 16 of the substrate 12, so that, when the forward side 38 of the package 14 is separated at the forward side weakened transverse line 50, a substantial portion of the central portion 20 is exposed. By "substantial portion" as used herein, it is meant that at least about 60% of the central portion 20 is exposed. Preferably, where the central portion is a soft pad, at least about 70% of the central portion 20 is exposed, more preferably at least about 80% is exposed, still more preferably at least about 80% is exposed, and most preferably the entirety of the central portion 20 is exposed.

Figure 6:
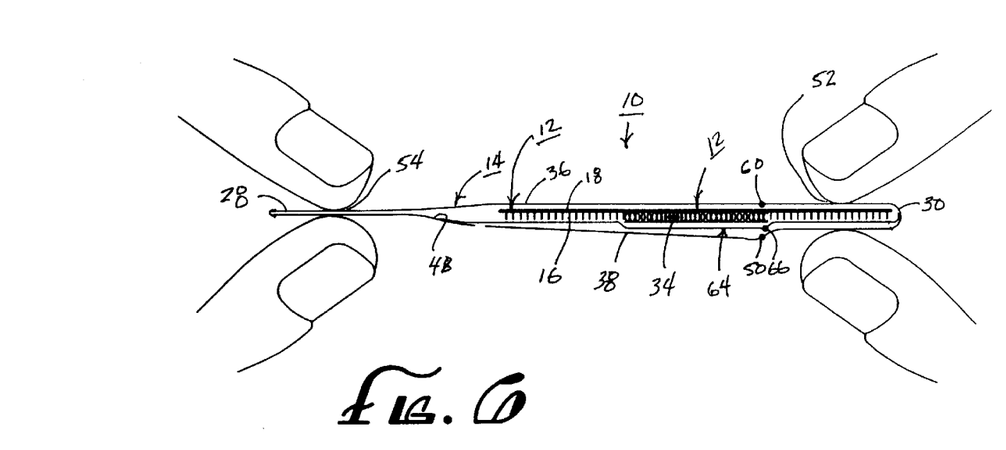
FIG. 6 is a side view in partial cross-section of a combination having features of the invention, including a self-adhesive bandage and an encompassing package.
Figure 7:
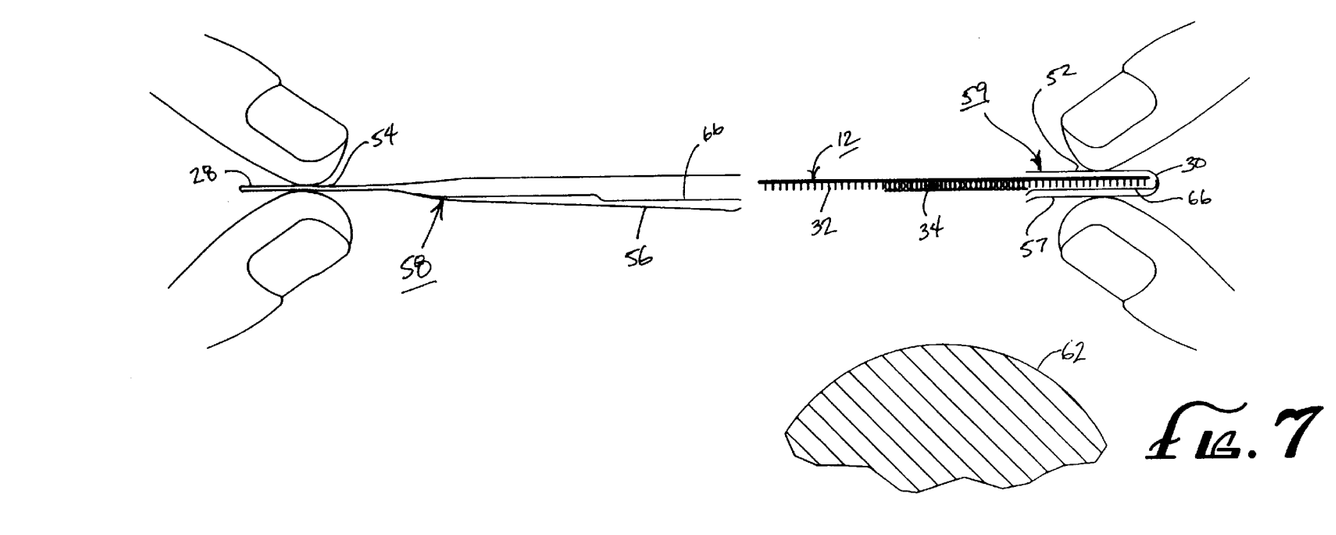
FIG. 7 is a side view in partial cross-section of the combination illustrated in FIG. 6, but depicted after the partial removal of the package from the self-adhesive bandage.

As illustrated in FIGS. 6 and 7, the invention 10 can further comprise an elongate non-stick sheet 64 disposed between the front side 16 of the substrate 12 and the forward side 38 of the package 14. The non-stick sheet 64 is composed of a material (or is coated with a material) which minimizes adhesion between the non-stick sheet 64 and the layers of adhesive 32 on the front side 16 of the substrate 12. In the embodiment illustrated in FIGS. 6 and 7, the non-stick sheet 64 has a non-stick sheet weakened transverse line 66 substantially aligned with the forward side weakened transverse line 50, so that the non-stick sheet separates 64 when the forward side 38 of the package 14 is separated.

Figure 8:
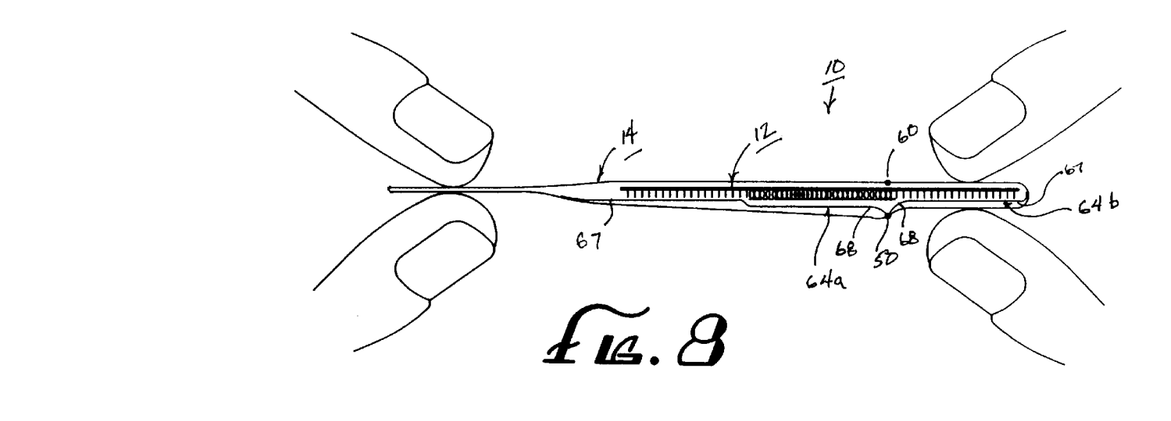
FIG. 8 is a side view in partial cross-section of another combination having features of the invention, including a self-adhesive bandage and an encompassing package.
Figure 9:
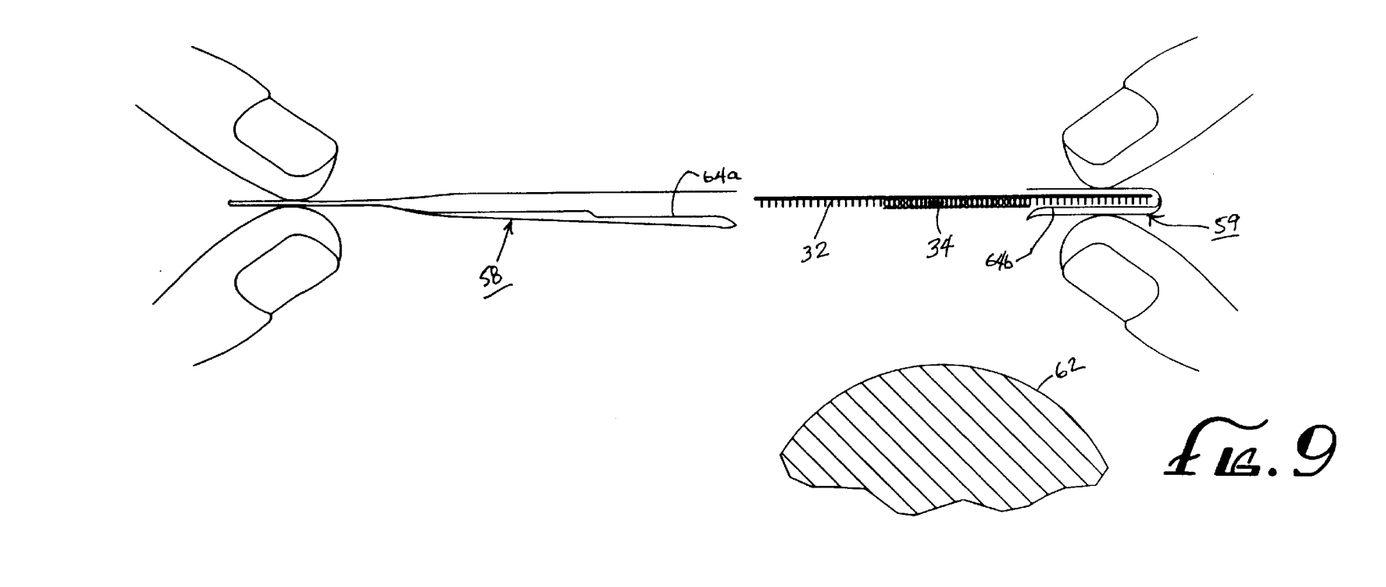
FIG. 9 is a side view and partial cross-section of the combination illustrated in FIG. 8, but depicted after the partial removal of the package from the self-adhesive bandage.

FIGS. 8 and 9 illustrate another embodiment of the invention 10. In this embodiment, the invention 10 comprises a pair of elongate non-stick sheet portions 64a and 64b disposed between the front side 16 of the substrate 12 and the forward side 38 of the package 14. Both non-stick sheet portions 64a and 64b are elongate and are disposed end to end so that the two non-stick sheet portions 64a and 64b cover the adhesive layer 32 on the front side 16 of the substrate 12. Both non-stick sheet portions 64a and 64b have distal ends 67 which are each disposed proximate to one of the distal ends 28 and 30 of the package 14. The proximal ends 68 of both non-stick sheet portions 64a and 64b are attached to the forward side 38 of the package 14 on opposite sides of the forward side weakened transverse line 50. By this design, the severing of the forward side weakened transverse line 50, followed by the separation of the two package moieties 56 and 57, necessarily peels back the two non-stick sheet portions 64a and 64b from the adhesive layers 32 on the front side 16 of the substrate 12.

Figure 10:
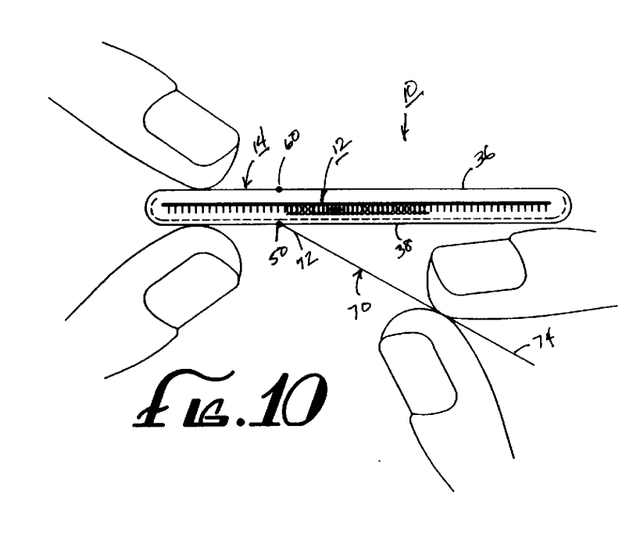
FIG. 10 is a side view in partial cross-section of yet another combination having features of the invention, including a self-adhesive bandage and an encompassing package.
Figure 11:
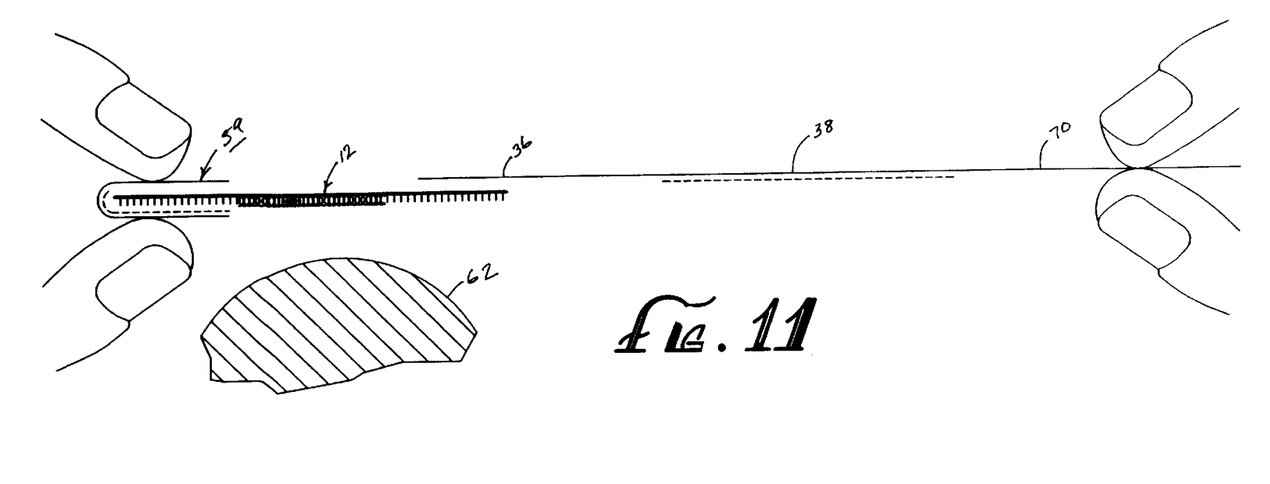
FIG. 11 is a side view and partial cross-section of the combination illustrated in FIG. 10, but depicted after the partial removal of the package from the self-adhesive bandage.

FIGS. 10 and 11 illustrate yet another embodiment of the invention 10. In this embodiment of the invention 10, the package 14 comprises a first pull tab 70. The first pull tab 70 has an attached end 72 and a free end 74. The attached end 72 is attached to the forward side 38 of the package 14 proximate to the forward side weakened transverse line 50. Preferably, the first pull tab 70 is attached to the forward side 38 of the package 14 such that pulling on the first pull tab 70 severs the forward side 38 of the package 14 at the forward side weakened transverse line 50 and peels back the longer of the two forward side moieties 56 away from the sterile pad 34 and one of the adhesive layers 32. This operation is further facilitated by a non-stick film disposed on the interior surface 48 of the forward side 38 of the package 14. Alternatively, one or more non-stick sheets 64 can be interposed between the adhesive layers 32 and the interior surface 48 of the forward side 38.

Figures 12, 13:
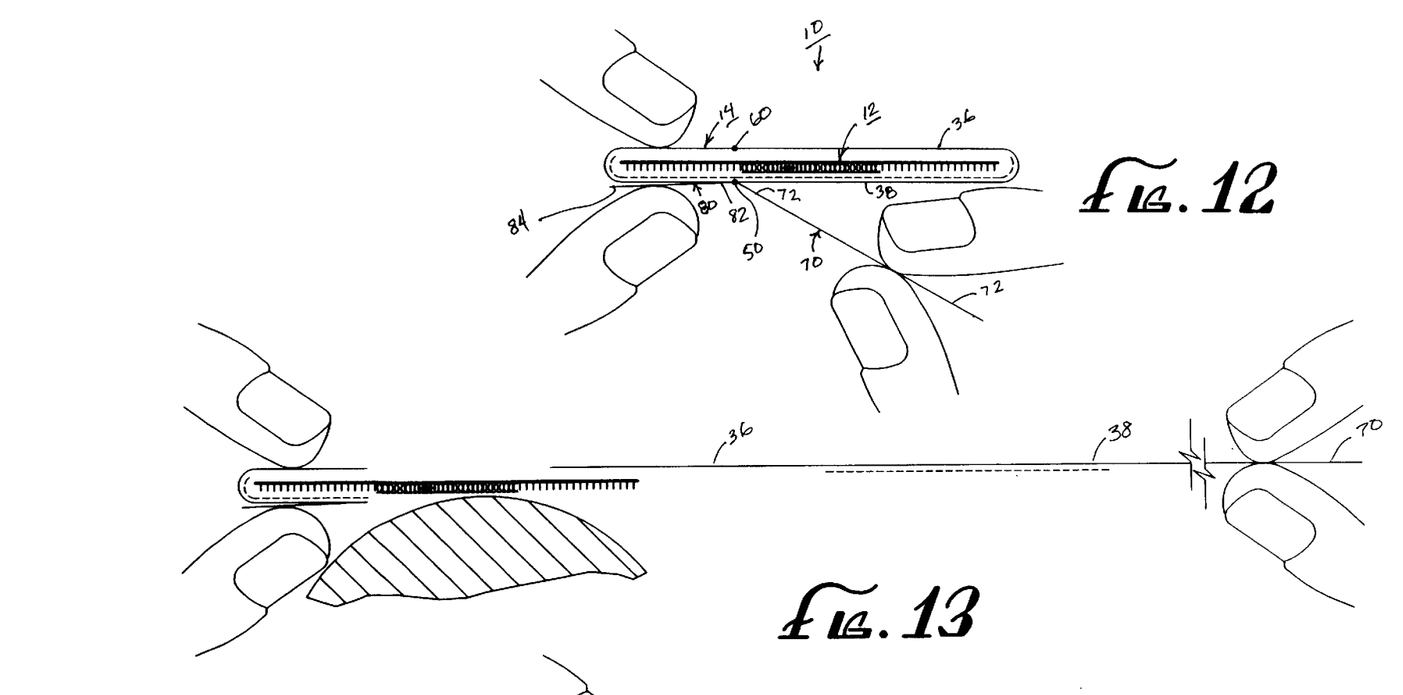
FIG. 12 is a side view in partial cross-section of still another combination having features of the invention, including a self-adhesive bandage and an encompassing package.
FIG. 13 is a side view and partial cross-section of the combination illustrated in FIG. 12, but depicted after the partial removal of the package from the self-adhesive bandage.
Figure 14:
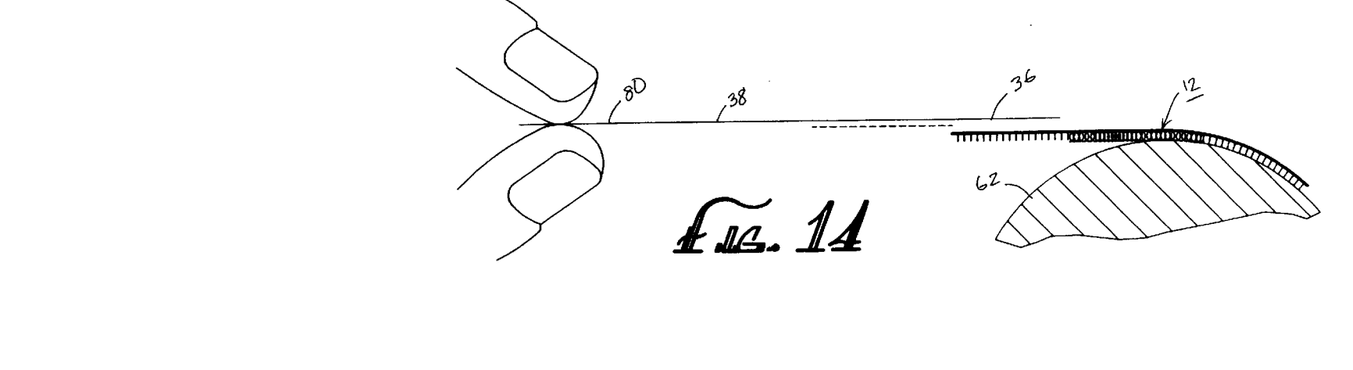
FIG. 14 is a side view and partial cross-section of the combination illustrated in FIG. 12, but depicted after the near-complete removal of the package from the self-adhesive bandage.

FIGS. 12–14 illustrate still another embodiment of the invention 10. In this embodiment, the package 14 comprises a pair of pull tabs, a first pull tab 70 and a second pull tab 80. Both pull tabs 70 and 80 have an attached end 72 and 82 and a free end 74 and 84. Both attached ends 72 and 82 are attached to the forward side 38 of the package 14 on opposite sides of the forward side weakened transverse line 50. By this design, the forward side moieties 56 and 57 of the package 14 can both be easily peeled away from both adhesive layers 32 on the front side 16 of the substrate 12 once the forward side weakened transverse line 50 is severed.

The operation of the embodiment illustrated in FIGS. 6 and 7 is as follows. The substrate 12 is a self-adhesive bandage, having adhesive-covered end portions 22 and a sterile soft pad 34 at its central portion 20. A user wishing to open the package 14 and gain access to the self-adhesive bandage 12 grips the package 14 at gripping locations 52 and 54 on opposite sides of the weakened transverse lines 50 and 60. As illustrated in FIG. 6, the user grips the larger of the two moieties 58 at the distal end 28 of that moiety 58 and grips the smaller of the two moieties 59 proximate to the weakened transverse lines 50 and 60. The user then pulls axially on the package 14 along the longitudinal axis 26. Such pulling effort causes the forward side 38 to separate at the forward side weakened transverse line 50, causes the rearward side 36 to separate at the rearward side weakened transverse line 60 and causes the non-stick sheet 64 to separate at the non-stick sheet weakened transverse line 66. This effectively severs the package 14 into the two separate moieties 58 and 59.

As the user continues to pull axially on the package moieties 58 and 59, the larger package moiety 58 is completely removed from the substrate 12 as illustrated in FIG. 7. The non-stick sheet 64 between the substrate 12 and the forward side 38 of the package 14 allows the larger package moiety 58 to strip easily off of the adhesive layer 32 on the end portion 22 of the substrate 12 originally retained within the larger package moiety 58. Because the forward side weakened transverse line 50 is disposed off-center with respect to the central portion 20 of the substrate 12, the removal of the larger package moiety 58 substantially exposes the sterile soft pad 34 and one of the two adhesive-coated end portions 22 is also exposed.

After the larger package moiety 58 is completely removed from the substrate 12, the user, while continuing to grip the smaller package moiety 59 proximate to the weakened transverse lines 50 and 60, can easily apply the bandage 12 to a wound 62 using only one hand. The user merely lays the soft sterile pad 34 against the wound 62 and smooths the adhesive 32 on the exposed end portion 22 against the skin of the user proximate to the wound 62. Having thus securing the bandage 12 to the wound 62, the user grips the smaller package moiety 59 at the distal end 30 and pulls the smaller package moiety 59 from the opposite end portion 22. As the user removes the package moiety 59 from the end portion 22, the adhesive 32 on the end portion 22 adheres to the skin of the user on the opposite side of the wound 62. The user has thus secured the bandage 12 to the wound 62 while retaining the bandage 12 with only one hand.

The operation of the embodiment illustrated in FIGS. 8 and 9 is similar to the operation of the embodiment illustrated in FIGS. 6 and 7. However, in the embodiment illustrated in FIGS. 8 and 9, as the user pulls axially on the package 14 along the longitudinal axis 26, the pulling effort causes the non-stick sheet portion 64a and 64b to peel away from the adhesive layers 32 on the first and second ends 22 and 24 of the substrate 12.

The operation of the embodiment illustrated in FIGS. 10–14 is similar to embodiments illustrated in FIGS. 6–9. However, in the embodiments illustrated in FIGS. 10–14, instead of pulling axially on both of the distal ends 28 and 30 of the package 14, the user pulls axially on one or both of the pull tabs 70 and 80 to sever the forward side weakened transverse line 50 and to peel away one or both of the forward side moieties 56 and 57 from the front side 16 of the substrate 12.

With all embodiments of the invention, the opening of the package 14 is accomplished without the awkwardness and difficulty inherent in prior art self-adhesive bandages. Moreover, all of the embodiments allow for the application of the bandage using only a single hand.

Having thus described the invention, it should be apparent that numerous structural modifications and adaptations may be resorted to without departing from the scope and fair meaning of the instant invention as set forth hereinabove and as described hereinbelow by the claims.

What is claimed is:

1. A combination of a planar substrate and a package for housing the substrate, the substrate having a front side and a back side, the front side comprising a central portion and opposed first and second end portions, the package being elongate and having a longitudinal axis and opposed first and second distal ends, the package further comprising:

(a) a rearward side proximate to the back side of the substrate;

(b) a forward side proximate to the front side of the substrate;

(c) a forward side weakened transverse line on the forward side, so that pulling on the package along the longitudinal axis from gripping locations on opposite sides of the forward side weakened transverse line causes the forward side to separate at the forward side weakened transverse line;

wherein the forward side weakened transverse line is disposed off center with respect to the central portion of the front side of the substrate, so that a substantial portion of the central portion is exposed by separating the forward side at the forward side weakened transverse line.

2. The combination of claim 1 wherein the forward side weakened transverse line is substantially perpendicular to the longitudinal axis of the package.

3. The combination of claim 1 further comprising a rearward side weakened transverse line on the rearward side of the package, so that pulling on the package along the longitudinal axis from gripping locations on opposite sides of the rearward side weakened transverse line causes the rearward side to separate at the rearward side weakened transverse line.

4. The combination of claim 3 wherein the forward side weakened transverse line and the rearward side weakened transverse line are substantially aligned.

5. The combination of claim 3 wherein both the forward side and rearward side weakened transverse lines are substantially perpendicular to the longitudinal axis of the package.

6. The combination of claim 1 wherein the forward side weakened transverse line is a thinned line.

7. The combination of claim 1 wherein the forward side weakened transverse line is a line of weakened material.

8. The combination of claim 7 wherein the weakened material is an adhesive.

9. The combination of claim 1, wherein the forward side of the package comprises an interior surface, and wherein the interior surface is coated with a low adhesive, non-stick film.

10. The combination of claim 1 further comprising an elongate non-stick sheet disposed between the rearward and forward sides of the package, the non-stick sheet having a non-stick sheet weakened transverse line substantially aligned with the forward side weakened transverse line.

11. The combination of claim 1 further comprising a pair of elongate non-stick sheets disposed between the forward and rearward sides of the package, both non-stick sheets being elongate and disposed end to end proximate to the forward side of the substrate, both non-stick sheets having a distal end and a proximal end, at least one proximal end of one of the two non-stick sheets being attached to the forward side of the package proximate to the forward side weakened transverse line.

12. The combination of claim 1 further comprising a pair of elongate non-stick sheets disposed between the forward and rearward sides of the package, both non-stick sheets being elongate and disposed end to end proximate to the forward side of the substrate, both non-stick sheets having a distal end and a proximal end, both proximal ends of the non-stick sheets being attached to the forward side of the package on opposite sides of the forward side weakened transverse line.

13. The combination of claim 1 wherein the forward side of the package further comprises a first pull tab having an attached end and a free end, the attached end being attached to the forward side of the package proximate to the forward side weakened transverse line.

14. The combination of claim 1 wherein the forward side of the package further comprises a first pull tab having an attached end and a free end and a second pull tab having an attached end and a free end, the attached ends of the two pull tabs being attached to the forward side of the package on opposite sides of the forward side weakened transverse line.

15. The combination of claim 1 wherein the central portion of the substrate comprises a soft pad.

16. The combination of claim 10 wherein at least 70% of the soft pad is exposed by separating the forward side of the package at the forward side weakened transverse line.

17. The combination of claim 10 wherein at least 80% of the soft pad is exposed by separating the forward side of the package at the forward side weakened transverse line.

18. The combination of claim 10 wherein at least 90% of the soft pad is exposed by separating the forward side of the package at the forward side weakened transverse line.

19. The combination of claim 10 wherein substantially the entirety of the soft pad is exposed by separating the forward side of the package at the forward side weakened transverse line.

20. A combination of a planar substrate and a package for housing the substrate, the substrate having a front side and a back side, the front side comprising a central portion with a soft pad and opposed first and second end portions, the package being elongate and having a longitudinal axis and opposed first and second distal ends, the package further comprising:

(a) a rearward side proximate to the back side of the substrate;

(b) a forward side proximate to the front side of the substrate;

(c) a forward side weakened transverse line on the forward side and a rearward side weakened transverse line on the rearward side, the forward side and the rearward side weakened transverse lines being substantially perpendicular to the longitudinal axis of the package and aligned with one another, so that pulling on the package along the longitudinal axis from gripping locations on opposite sides of the weakened transverse lines causes the forward side to separate at the forward side weakened transverse line and the rearward side to separate at the rearward side weakened transverse line, wherein the forward side weakened transverse line is disposed off center with respect to the soft pad, so that at least 80% of the soft pad is exposed by separating the forward side at the forward side weakened transverse line.

* * * * *